US009179858B2

(12) United States Patent
Hasson et al.

(10) Patent No.: US 9,179,858 B2
(45) Date of Patent: Nov. 10, 2015

(54) COMPUTER-ACCESSIBLE MEDIUM, SYSTEM AND METHOD FOR ASSESSING EFFECT OF A STIMULUS USING INTERSUBJECT CORRELATION

(75) Inventors: Uri Hasson, Princeton, NJ (US); Rafi Malach, Tel Aviv (IL); David Heeger, Montclair, NJ (US)

(73) Assignees: New York University, New York, NY (US); Yeda Research and Development Co. Ltd. at the Weizmann Institute of Science, Rehovot (IL)

( * ) Notice: Subject to any disclaimer, the term of this patent is extended or adjusted under 35 U.S.C. 154(b) by 1270 days.

(21) Appl. No.: 12/921,076

(22) PCT Filed: Mar. 5, 2009

(86) PCT No.: PCT/US2009/036212
§ 371 (c)(1),
(2), (4) Date: Mar. 21, 2011

(87) PCT Pub. No.: WO2009/111652
PCT Pub. Date: Sep. 11, 2009

(65) Prior Publication Data
US 2011/0161011 A1     Jun. 30, 2011

Related U.S. Application Data

(60) Provisional application No. 61/034,033, filed on Mar. 5, 2008.

(51) Int. Cl.
*A61B 5/055* (2006.01)
(52) U.S. Cl.
CPC ..................................... *A61B 5/055* (2013.01)
(58) Field of Classification Search
CPC ............ A61B 5/055; A61B 5/05; A61B 5/00; A61B 5/16; A61B 5/0488; A61B 5/0484; A61B 5/04842; A61B 5/04845; A61B 5/04847; A61B 5/12; A61B 3/113; G06F 17/00

USPC .............................. 702/182; 705/14.41–14.43
See application file for complete search history.

(56) References Cited

U.S. PATENT DOCUMENTS 5,243,517 A     9/1993  Schmidt et al.
5,676,138 A  * 10/1997  Zawilinski ..................... 600/301
(Continued)

OTHER PUBLICATIONS

International Search Report and Written Opinion for PCT/US2009/036212 dated Aug. 14, 2009.
(Continued)

*Primary Examiner* — Manuel L Barbee
(74) *Attorney, Agent, or Firm* — Andrews Kurth LLP

(57) ABSTRACT

Exemplary embodiments of a system and method can be provided for measuring a level and/or details of how engaging, effective or memorable a stimulus that may be based on information associated with one or more subjects' neuronal, physiological and/or behavioral responses to the stimulus. In addition, an exemplary embodiment of a computer-accessible medium containing executable instructions thereon can also be provided which can be executed by a processing arrangement. For example, when the processing arrangement executes the instructions, the processing arrangement can be configured to, e.g., receive neuronal, physiological and/or behavioral data one or more subjects being presented with stimuli, determine further data associated with a measure of inter-subject similarity of the neuronal, physiological and/or behavioral data, and identify particular portions of the stimuli that meet a pre-determined criteria relating to the further data associated with the measure of inter-subject similarity. In addition, the processing arrangement can be further configured to display and/or store identifiers of the particular portions of the stimuli in a storage arrangement in a user-accessible format and/or a user-readable format.

40 Claims, 11 Drawing Sheets

(56) References Cited

U.S. PATENT DOCUMENTS

| | | | |
|---|---|---|---|
| 6,099,319 A | * | 8/2000 | Zaltman et al. ............... 434/236 |
| 6,102,873 A | * | 8/2000 | Claessens ..................... 600/595 |
| 6,228,038 B1 | * | 5/2001 | Claessens ..................... 600/558 |
| 6,585,521 B1 | | 7/2003 | Obrador |
| 2009/0083129 A1 | * | 3/2009 | Pradeep et al. ................. 705/10 |

OTHER PUBLICATIONS

Uri Hasson et al. "Intersubject Synchronization of Cortical Activity During Natural Vision" Science, vol. 303 (2004) pp. 1634-1640.

* cited by examiner

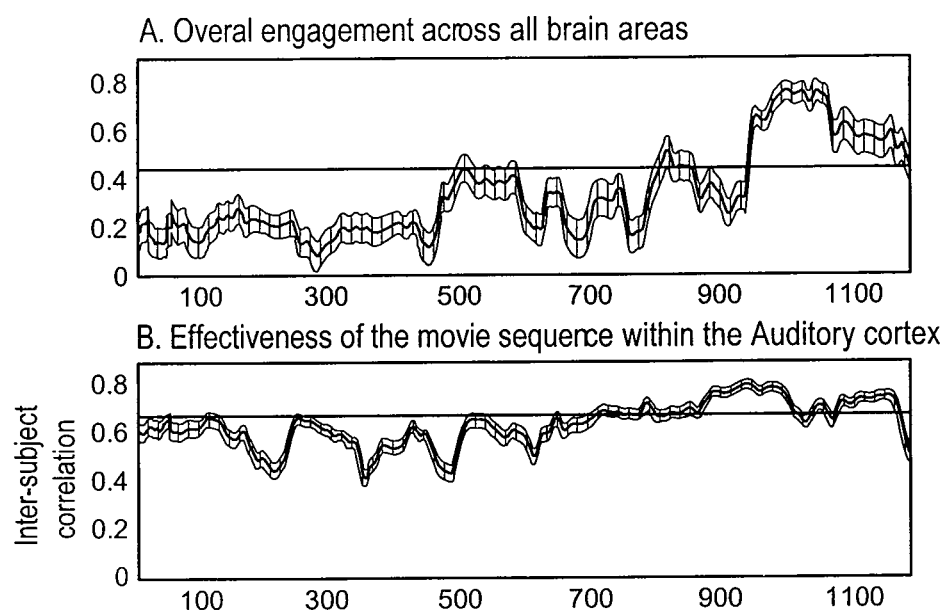
F I G. 8
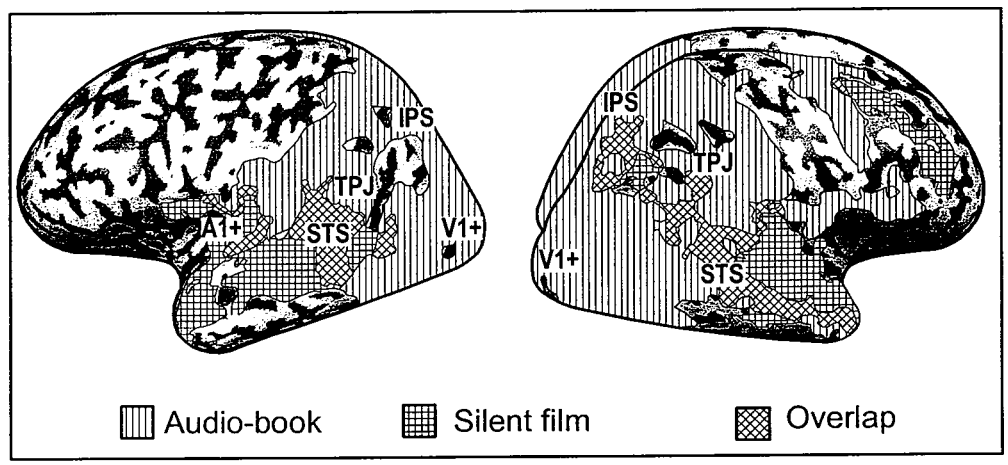
F I G. 9

COMPUTER-ACCESSIBLE MEDIUM, SYSTEM AND METHOD FOR ASSESSING EFFECT OF A STIMULUS USING INTERSUBJECT CORRELATION

CROSS-REFERENCE TO RELATED APPLICATION

The present application is a U.S. National Phase of International Application PCT/US2009/036212 filed Mar. 5, 2009, and also claims priority from U.S. patent application Ser. No. 61/034,033, filed Mar. 5, 2008, the entire disclosures of which are hereby incorporated herein by reference in their entireties.

FIELD OF THE INVENTION

The present disclosure relates to computer accessible medium, systems and methods for measuring a level of and/or details regarding how engaging, effective and/or memorable a stimulus is based on information associated with one or more subjects' neuronal, physiological and/or behavioral responses to the stimulus.

BACKGROUND INFORMATION

A stimulus can commonly be associated with popular media that may typically include one or more complex sequences of audio and/or visual stimuli, for example. Such stimuli can include, e.g., films, speeches, trailers, television (TV) programs, advertisements, video clips and/or features, audio books, and music. Neuronal responses can be obtained using various measurement techniques including, e.g., functional magnetic resonance imaging (fMRI), positron emission tomography (PET), single photon emission computed tomography (SPECT), functional near-infrared spectroscopy (fNIRS), optical imaging (e.g., of intrinsic signals and/or voltage-sensitive fluorescent dyes), electroencephalography (EEG), and magnetooencephalography (EEG). Other physiological and/or behavioral measurements can include, e.g., galvanic skin response (GSR), eye movements, pupil size, and motion capture of head movements, body movements and facial expressions. Such types of spatiotemporal stimuli may evoke complex non-linear neurophysiological responses that can be difficult to decode. For example, a common challenge is to extract from the complex spatiotemporal response patterns a physiological marker that can indicate the engaging power of a stimulus, the degree to which such stimulus is absorbed, and/or the cognitive and/or emotional effectiveness of the stimulus, for example.

Various neuroimaging techniques have been used in research laboratories to expand humans' knowledge of the human brain and mind. However, this research generally follows a reductionistic type of deductive line of reasoning. Previously, neuroscientists have worked toward simplification, using simple precisely parameterized stimuli and behavioral tasks in highly controlled laboratory settings. This type of approach yielded certain knowledge about human brain structure and functionality. However, such basic science laboratory research experiments generally did not yield specific knowledge of human brain structure and functionality applicable in real-word situations (e.g., outside of research laboratories); despite it having been suggested to use neuroimaging methods (e.g., fMRI), physiological methods (e.g., GSR) and/or behavioral methods (e.g., eye tracking) to assess responses to real-world stimuli and popular media.

Accordingly, there may be a need to overcome at least some of the above-described deficiencies, and provide exemplary embodiments of computer accessible medium, systems and methods for measuring a level of and/or details regarding how engaging, effective and/or memorable a stimulus is based on information associated with one or more subjects' neuronal, physiological and/or behavioral responses to the stimulus, the examples of which are described herein.

SUMMARY OF EXEMPLARY EMBODIMENTS

It is one of the objects of the present disclosure is to provide exemplary embodiments of a computer-accessible medium containing executable instructions thereon. For example, when a processing arrangement executes the instructions, the processing arrangement can be configured to, e.g., receive neuronal, physiological and/or behavioral data one or more subjects being presented with stimuli, determine further data associated with a measure of inter-subject similarity of the neuronal, physiological and/or behavioral data, and identify select portions of the stimuli that meet a pre-determined criteria relating to the further data associated with the measure of inter-subject similarity. In addition, the processing arrangement can be configured to display and/or store identifiers of select portions of the stimuli in a storage arrangement in a user-accessible format and/or a user-readable format.

The physiological and/or behavioral data can be, e.g., MRI, PET, SPECT, fNIRS, optical imaging, EEG, MEG, GSR, eye movements, pupil size, and/or a motion capture of head movement, body movement and/or facial expression, for example. The stimuli can, e.g., include visual, auditory, tactile, olfactory and/or gustatory stimuli. The measure of inter-subject similarity can be determined using, e.g., a correlation, a general linear model, a canonical correlation, a coherence, a mutual information, a posterior cerebral artery (PCA) or an independent component analysis (ICA).

The stimuli can be a recorded stimuli having a form of, e.g., an audio recording, a film, a video and/or an advertisement. The identifiers can include one or more frame numbers and/or one or more points in time referencing select portions of, e.g., an audio recording, a film, a video or an advertisement, for example. The identifiers can be configured to provide to a user and/or a computer system access to portions of, e.g., a film and/or video, whereas the access can provide the capability to edit and/or alter the portions of the film and/or a video, for example.

The measure of the inter-subject similarity can relate to an activity of e.g., a visual cortex, an auditory cortex, a language area, an anterior cingulate, an anterior dorsolateral prefrontal cortex, a posterior dorsolateral prefrontal cortex, a frontal eye field, a medial prefrontal cortex, an orbito-frontal cortex, a fusiform face area, a parahippoampal place area, a lateral occipital cortex, a lateral occipital face area, an MT complex, a superior temporal sulcus, a superior temporal face area, a temporal pole, a temporal-parietal junction, an intraparietal sulcus, a mirror system area, a precuneus, a ventral premotor area, a dorsal premotor area, a medial temporal lobe, a hippocampus, an entorhinal cortex, a perirhinal cortex, an amygdala, a basal ganglia, a striatum, a putamen, a caudate, a pallidum, a substantia nigra and/or a cerebellum of a brain of one or more subjects. For example, the measure of the inter-subject similarity can be obtained independently of a reliance on a particular regional functional specialization of a brain.

The processing arrangement can be further configured to compare between the select portions for two or more demographic groups of subjects. Select portions of the stimuli can be used to assess, e.g., memorability, engagement, effectiveness, cognition and/or an emotional response. For example, the select portions of the stimuli can be selected as a function of a percentage of a cortex that meets a predetermined criteria of a similarity. The select portions of the stimuli can be selected as a function of a magnitude of a similarity in a plurality of brain areas, for example. The select portions of the stimuli can be selected based on, e.g., a sequence of movie scenes and/or video scenes with overlapping and/or non-overlapping time windows, for example, and the similarity may be measured separately for, e.g., one or more scenes of a movie and/or one or more time windows.

According to another exemplary embodiment of the present disclosure, a system for measuring a level and/or details of how engaging, effective or memorable a stimulus can be provided which is based on information associated with one or more subjects' neuronal, physiological and/or behavioral responses to the stimulus. The exemplary system may comprise a computer-accessible medium having executable instructions thereon. For example, when a processing arrangement executes the instructions, the processing arrangement can be configured to, e.g., receive a physiological and/or behavioral data of one or more subjects being presented with stimuli, determine further data associated with a measure of inter-subject similarity of the physiological and/or behavioral data, and identify select portions of the stimuli that meet a pre-determined criteria relating to the further data associated with the measure of inter-subject similarity. In addition, the processing arrangement can be configured to display and/or store identifiers of select portions of stimuli in a storage arrangement in a user-accessible format and/or a user-readable format. The physiological and/or behavioral data can be, e.g., MRI, PET, SPECT, fNIRS, optical imaging, EEG, MEG, GSR, eye movements, pupil size, and/or a motion capture of head movement, body movement and/or facial expression, for example.

Further, according to yet another exemplary embodiment of the present disclosure, a method can be provided for measuring a level and/or details of how engaging, effective and memorable a stimulus is based on, e.g., information associated with one or more subjects' neuronal, physiological and/or behavioral responses to the stimulus. The example method can comprise, e.g., receiving physiological and/or behavioral data of one or more subjects being presented with stimuli; using a processing arrangement, automatically determining further data associated with a measure of inter-subject similarity of the physiological and/or behavioral data; using the processing arrangement, and automatically identifying select portions of the stimuli that meet a predetermined criteria relating to the further data associated with the measure of inter-subject similarity. Further, the exemplary method can also display and/or store identifiers of select portions of the stimuli in a storage arrangement of a user-accessible format and/or a user-readable format. For example, the physiological and/or behavioral data can be, e.g., MRI, PET, SPECT, fNIRS, optical imaging, EEG, MEG, GSR, eye movements, pupil size, and/or a motion capture of head movement, body movement and/or facial expression.

BRIEF DESCRIPTION OF THE DRAWINGS

Further objects, features and advantages provided by the present disclosure will become apparent from the following detailed description taken in conjunction with the accompanying figures showing illustrative embodiments, in which:

FIG. 8 is a set of exemplary graphs illustrating an example evolution of an exemplary inter-subject correlation over time in accordance with exemplary embodiments of the present disclosure;

FIG. 9 is a set of exemplary images of exemplary inter-subject correlations for a visual image and an audio soundtrack in accordance with exemplary embodiments of the present disclosure;

Figure 1:
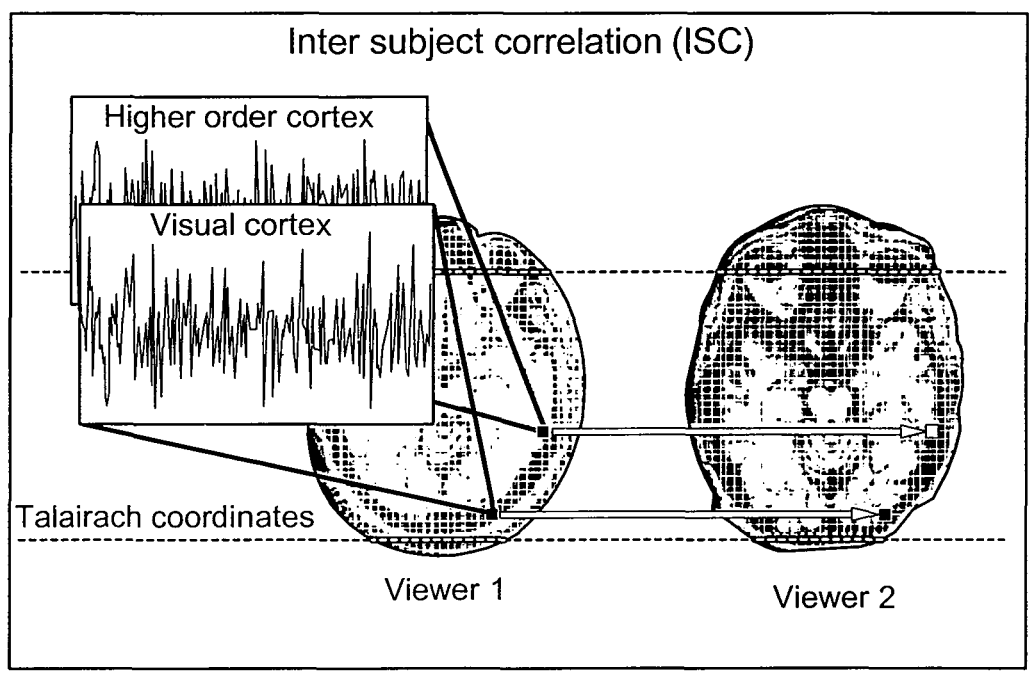
FIG. 1 is an exemplary image generated by an exemplary embodiment of an inter-subject correlation (ISC) analysis procedure in accordance with the present disclosure.

Throughout the figures, the same reference numerals and characters, unless otherwise stated, are used to denote like features, elements, components or portions of the illustrated embodiments. Moreover, while the present disclosure will now be described in detail with reference to the accompanying figures, it is done so in connection with the illustrative embodiments. It is intended that changes and modifications can be made to the described embodiments without departing from the true scope and spirit of the present disclosure.

DETAILED DESCRIPTION OF EXEMPLARY EMBODIMENTS

Exemplary embodiments according to the present disclosure relate to, but differ from, conventional analysis of event related potentials (ERP), electroencephalographic (EEG), magnetooencephalographic (MEG), and functional magnetic resonance imaging (fMRI) devices. As discussed herein, exemplary embodiments in accordance with the present disclosure do not have to characterize response patterns or time courses for a given measurement method, and do not have to search for generalizable response patterns and/or time courses which may signal the effectiveness of one or more stimuli. Further, exemplary embodiments in accordance with the present disclosure do not have to be based on averaged ERPs, averaged EEG responses, averaged MEG responses, or averaged fMRI responses, for example, and can be based on continuous response patterns over an entire presentation.

In addition, exemplary embodiments in accordance with the present disclosure do not have to rely on a functional specialization hypothesis. Existing methods generally assume knowledge of a functional specialization and/or cognitive function of localized brain areas. Further, certain existing methods rely on a need to characterize in advance the functional role of one or more specific brain areas. Moreover, associated neuroimaging based systems and processes that rely on a need to characterize in advance the functional role of one or more specific brain areas tend to have the following drawbacks and/or deficiencies:

A. The concept that specific brain areas have unique functional specialization (e.g., that activity in a specific brain area corresponds to a specific cognitive function) is a hypothesis (i.e., not factual). Although there is evidence for functional specialization on a broad coarse scale (e.g., vision versus motor control versus reward systems in the brain), there is actually little evidence for functional specialization on a finer scale, which is commonly required for related existing and previously proposed methods, systems and processes. Thus, in order for the existing and previously proposed methods, systems and processes to work, it would likely be necessary to first know how to interpret activity in specific brain areas with respect to such brain areas' function to infer attitudes, engagement, preferences, and opinions, for example. Accordingly, the basic concepts of these existing proposed methods, systems and processes tend to rely on scientific hypotheses that have not yet been proven.

B. Even if such a hypothesis is correct, a significant period of time may pass before it is possible to confidently assign a functional label to each of the relevant brain areas, which can consequently severely limit the accuracy and/or applicability of existing and proposed methods, systems and processes.

C. It can be generally presumed and widely accepted that certain specific brain areas are involved with more than one brain-activity function, which further compromises accuracy and/or applicability of existing and proposed methods, systems and processes.

D. Further, even if it was possible to assign a functional label to specific brain areas, existing technologies are still far from being able to characterize appropriate response patterns associated with a subject's mental state. For example, a given behavioral effect (e.g., being engaged with a movie) may be associated with a number of different types of activation profiles (e.g., enhancement and/or reduction in response amplitudes).

E. Moreover, to prove that a certain neural response pattern is indicative of a specific cognitive function, it may be important to identify a well-characterized neurophysiological marker which can be generalized across different stimuli and contexts, and predict a level of effectiveness of each individual stimulus. However, no such generalized neurophysiological markers have been previously demonstrated.

The functional properties of brain areas can be considered as being far from known, and the notion that activation of specific brain areas is associated solely or primarily with the emotional value of specific stimuli is simplistic and deficient. Even if there was a strong link between the emotional value and the activation patterns in specific brain areas, existing technologies are still far from being able to read out such information from complex spatio-temporal response patterns that may be associated with specific stimuli. Accordingly, the conventional existing and previously-proposed conceptual methods, systems and processes go far beyond the generally accepted proven facts, and indeed generally conflict with basic principles of brain function and organization, which may be why people having ordinary skill in the art have not yet been able to successfully implement such conceptual methods, systems and/or processes.

According to various embodiments in accordance with the present disclosure, computer-accessible medium, system and method can be provided to facilitate an inter-subject correlation for measuring a level of and/or details regarding how engaging, effective and/or memorable a stimulus is based on information associated with one or more subjects' neuronal, physiological and/or behavioral responses to the stimulus. For example, instead of attempting to identify a well characterized and relatively simple neurophysiological marker for assessing the effectiveness of popular media, it is possible to implement an inter-subject correlation (ISC) procedure to measure the extent to which brain areas show consistent activation patterns across a plurality of subjects (e.g., across all subjects or across subjects in a particular demographic group) in response to a particular stimulus.

The level of ISC in a specific brain area can be a measure of the similarity of the processing within that brain area across viewers in a sample group. For example, high correlation across subjects in early visual and/or auditory associated brain areas indicates that the particular visual and/or auditory stimuli are effective in eliciting the same neuronal processes in these areas across all subjects. It is not necessary to first know what function is associated with each brain area. Rather, even if the function of a brain area is unknown, it is possible to measure the ISC. Moreover, it is not necessary to presume that activity in any particular brain area increases when viewers are more engaged. High ISC can occur because of similar modulations (e.g., increases and decreases) of activity over time across subjects.

Described herein are two exemplary implications of determining that a stimulus (e.g., a movie) can evoke similar modulations of brain activity across a plurality of viewers (subjects). First, e.g., certain stimuli have the potency to "control" viewers' neural responses. As used in this context, "control" can mean, but is certainly not limited to, that the sequence of neural states evoked by the stimulus may be relatively reliable, predictable and common for most or all viewers without placing any aesthetic or ethical judgment as to whether such control is desirable, for example. Second, under the presumption that mental states are tightly related to brain activity states, controlling viewers' brain activity states can be considered virtually the same as controlling their mental states including their percepts, emotions, thoughts, attitudes, etc.

For example, a calculation or determination of the degree of ISC within a specific brain area (e.g., the auditory cortex) can serve as a measurement of the effectiveness of a specific stimulus (e.g., a soundtrack) to induce similar response patterns across all subjects exposed to the same stimulus. The anatomical extent of high ISC across the brain can serve as a global measurement as to the collective engagement power of a specific stimulus.

The higher the correlation across subjects in a specific brain area, the more effective a particular stimulus can be for that particular brain area. For example, a high ISC in visual areas of the brain in response to a given visual stimulus (e.g., movie) can mean that the visual images elicit a common response modulation across all viewers (e.g., a particular stimulus may be highly effective in controlling the visual percepts of all viewers). Likewise, a high ISC in auditory areas of the brain can mean that a sound track is highly effective in controlling the auditory percepts of most or all viewers. Moreover, the ISC in emotional and cognitive areas of the brain can reveal the effectiveness of popular media in controlling viewers' emotions and thought processes, respectively. Furthermore, the ISC in memory related brain regions, including, e.g., the medial temporal lobe parahippocampal gyrus and the medial prefrontal cortex, can provide a reliable index of the memorability of events presented in a given popular media.

Accordingly, an exemplary embodiment of an ISC procedure according to the present disclosure can differ from heretofore existing and previously-proposed conventional analyses in several ways, for example, as follows:

A. The ISC procedure may not require any prior knowledge of an expected brain signal to a given stimulus. Thus, the exemplary ISC procedure can detect all reliable response patterns across all subjects or across any subgroup of subjects and cortical areas without the need for any presumptions as to their exact functional properties.

B. The exemplary ISC procedure can be optimally suited to a natural, continuous stream of information, which can be important elements of most, if not all, popular media (e.g., movies, music, TV programs, commercials, etc.). In contrast, the existing technologies may be optimized for unnatural stimulus-response paradigms in which a brief stimulus is presented, and the evoked response to that discrete stimulus is then measured.

C. The exemplary ISC procedure does not have to presume that the response patterns will be similar across different stimuli, and does not rely on a need to characterize the common properties in the response patterns that will be shared by most, if not all, stimuli. For example, one movie may be engaging because it evokes high ISC in areas of the brain that process fear and anxiety whereas another movie might be engaging because it evokes high ISC in areas of the brain that process humor.

D. The ISC can assess the effectiveness of each stimulus for different target groups by computing the ISC separately for each group.

The ISC procedure does not require data reduction but rather can be utilized through assessing the ISC for the entire spatio-temporal pattern of brain activity across subjects.

Indeed, according to various exemplary embodiments in accordance with the present disclosure, the ISC procedure used in concert with the exemplary embodiments of the computer-accessible medium, systems and methods according to the present disclosure can be used for measuring the extent to which spatiotemporal brain responses are similar across different individuals exposed to the same material. Such exemplary embodiments can provide new ways for assessing the level of control a given media has upon viewers' minds.

For example, various exemplary embodiment of an ISC analysis can be used as a tool and/or procedure for assessing both collective engagement and effectiveness of popular media. First, e.g., a collective engagement can be reflected in the ability to produce high ISC in as many brain regions as possible. No presumptions about the functional specialization of any particular brain area is needed. Second, e.g., the level of effectiveness of each dimension of the stimulus (e.g., image, sound track, narrative, thoughts, emotions etc.) can be reflected in the degree of ISC within each brain area that specializes in processing each of such given dimensions. Third, e.g., high ISC in high-order cognitive areas may be indicative of the effectiveness of the stimulus for controlling thought processes. Fourth, e.g., high ISC in the medial temporal lobe and other memory-related brain areas can be predictive of what subjects will remember. Fifth, e.g., high ISC in emotion-related brain areas can be predictive of subjects' emotional responses. Sixth, different target groups may respond differently to the same stimulus, thus the exemplary embodiment of the ISC procedure can be used to detect whether a given stimulus is effective for a given target group. Seventh, a time varying version of the exemplary ISC procedure can assess separately the effectiveness of each segment of a particular stimulus, such as a movie, for example.

Exemplary embodiments in accordance with the present disclosure that can utilize the exemplary ISC by the exemplary computer-accessible medium, systems and methods which can implement certain example ISC procedures are described herein. For example, an example of the ISC procedure can include, among other things, a procedure or a set of procedures which can be implemented using several computational methods and systems (e.g., correlation, coherence, mutual information, principal components analysis, independent components analysis, canonical correlation, general linear model, etc.) on different types of neurophysiological (e.g., fMRI, EEG, PET, fNIRS, etc.) physiological (e.g., GSR, etc.), and behavioral (e.g., eye movements, etc.) signals, to assess the effectiveness of different types of stimuli such as popular media (e.g. music, films, ads, audio-books, speeches).

Exemplary Computational Procedure of an ISC

In accordance with an exemplary embodiment of the ISC computational procedure, it is possible to measure brain activity using fMRI during free viewing of movies. For example, "free viewing" can mean in this context, but is not limited to, that participating subjects have the option of looking at anything that each of them may choose during, e.g., a movie presentation. The subjects can have the option of closing their eyes, or ending the movie and getting out of the scanner at any time during the example procedure. The fMRI data may be processed by computationally registering each viewer's brain into what is known as the Talairach coordinate system so that corresponding regions of each brain may be roughly aligned with one another, spatially smoothing the data to overcome any residual misregistration between brains, and then correlating the response time courses in a given brain region across viewers (see exemplary illustration as shown in FIG. 1 and described below).

In particular, FIG. 1 shows an illustration of an image generated using an exemplary embodiment of the inter-subject correlation analysis in accordance with the present disclosure. The exemplary inter-subject correlation procedure can measure the similarity in brain activity across viewers by comparing the response time course in each brain region from one viewer (e.g., Viewer 1 in FIG. 1) with the response time courses obtained in the same brain region from other viewers (e.g., Viewer 2) while being exposed to one or more stuimulus (e.g., while watching a movie).

Figure 2:
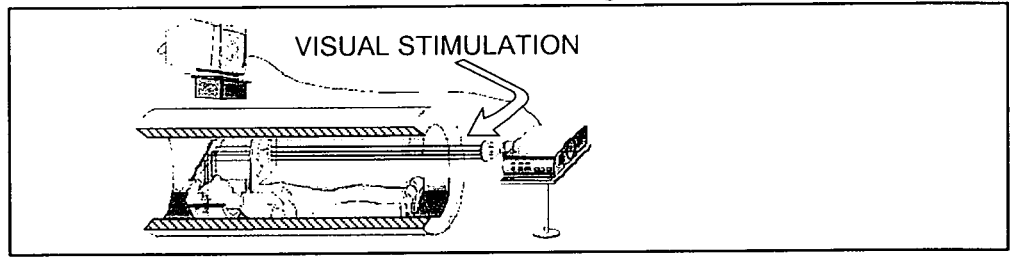
FIG. 2 is an illustration of two diagrams of an exemplary embodiment of a procedure using functional magnetic resonance imaging (fMRI) to measure inter-subject correlation for a film in accordance with the present disclosure.
Figure 2:
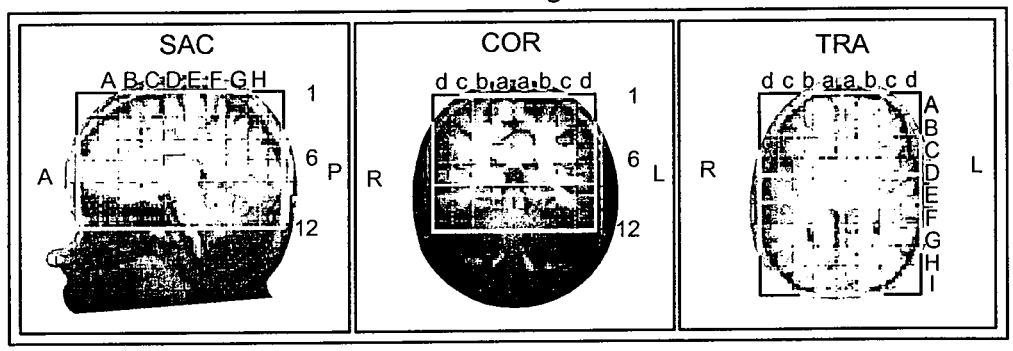
Figure 2:
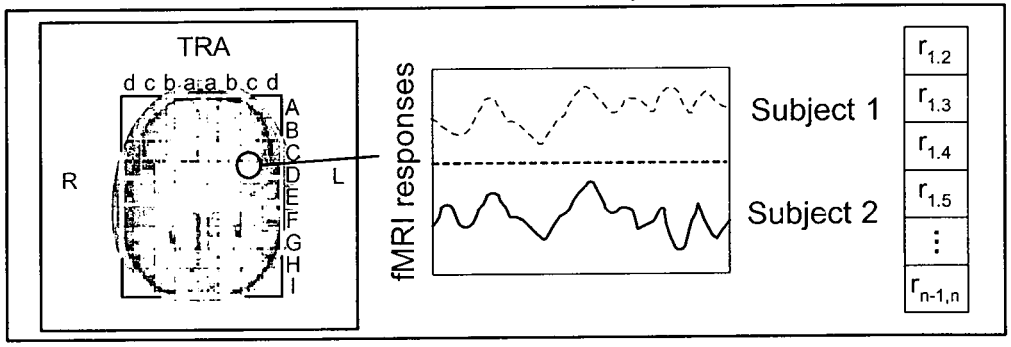
Figure 2:
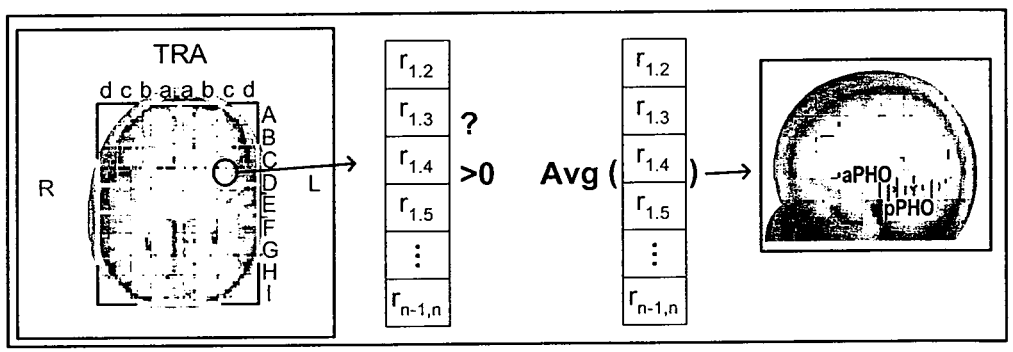

For example, according to various exemplary embodiments, the inter-subject correlation procedure can include the computational procedures shown in FIG. 2, which illustrates an exemplary procedure that can use fMRI technique(s) to measure the exemplary ISC for a film. With respect to the fMRI scanning (I), a number of volunteers may be recruited to participate, each of which watches (free-viewing) a movie (or a segment from a movie) while lying in an MRI scanner. Functional MRI data can be acquired continuously while the volunteers watch the movie. During this time, the volunteers may be asked to hold still. Anatomical images (e.g., images of brain structure) are also obtained, either before or after movie watching.

The anatomical images of each subject's brain can then be computationally registered to what is known as the Talairach coordinate system so that corresponding regions of each brain are roughly aligned with one another (II). There are several possible alternatives to the Talairach coordinate system that can be used, including, e.g., MNI space and surface-based alignment, which can also facilitate aligning the data from each subject to one another. For each subject, the cortical surface can also be reconstructed from the anatomical images and computationally flattened, which is not necessary but can aid in visualizing the data). The fMRI data can be processed by high-pass filtering to remove slow (low frequency) drift over time and, 3D-motion correction to compensate for any residual head motion. Other spatial smoothing of the data can be used to overcome any residual misregistration between brains.

For each voxel, an exemplary inter-subject correlation can be determined or computed for each pair of subjects via a pair-wise inter-subject correlation analysis (III). The exemplary procedure can be repeated on a voxel-by-voxel basis for all subject pairs resulting in a set of correlation coefficients for each voxel.

Statistical parametric mapping (IV) can then be used so that for each voxel, the average correlation coefficient (r) can be calculated, after applying a Fisher transformation to individual correlation coefficients, for example. To prevent these mean correlation values from being biased by outliers, a second order t-test analysis can be performed on the pair-wise values to confirm that the mean value is significantly different from zero. These mean correlation values may reflect the degree of similarity of the response pattern in each region between subjects.

Figure 3:
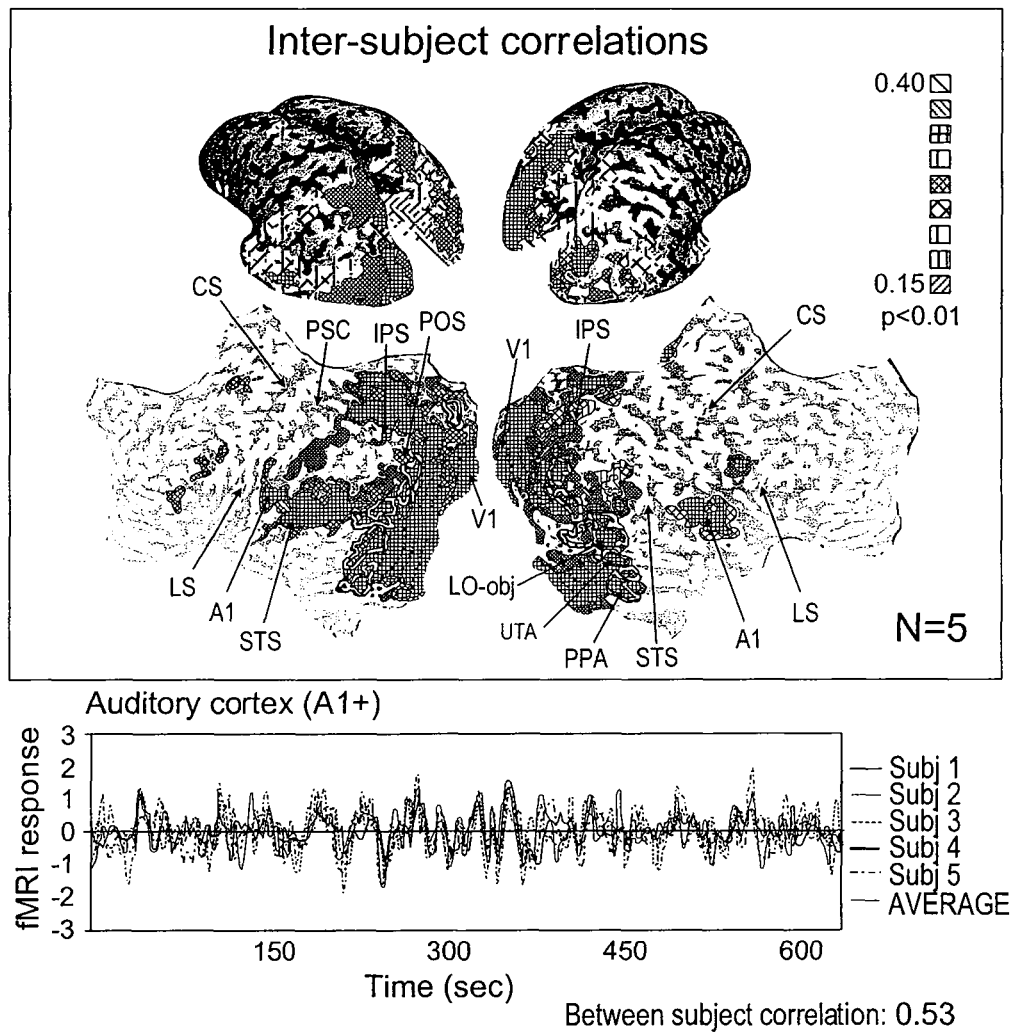
FIG. 3 is an illustration of portions of subject's brain and neural activity, and another illustration of exemplary graphs obtained using inter-subject correlation in accordance with exemplary embodiments of the present disclosure.

FIG. 3 shows an example of images generated using the exemplary ISC procedure for one example movie (e.g., "The Good, the Bad, and the Ugly"). As can be seen in FIG. 3, the example ISC reveals that approximately 30%-40% of the cerebrum responded similarly across neurotypical individuals while watching the movie. As illustrated, for example, in FIG. 3, an average (N=5) inter-subject correlation parametric map is shown as being provided across all pair-wise comparisons. Exemplary correlation maps are shown for inflated and flattened left and right brain hemispheres. As illustrated, outlines indicating high-level visual areas that respond preferentially to faces, objects and buildings are shown by the different shaded rings, respectively, as well as dotted lines indicating borders of retinotopic visual areas (e.g., V1, V2, V3, VP, V3A, V4). The bottom portion of FIG. 3 illustrates an example average time course sampled from a representative brain area (e.g., auditory cortex) for all five subjects, which shows a strikingly similar reproducibility of the spatio-temporal response.

Figure 4:
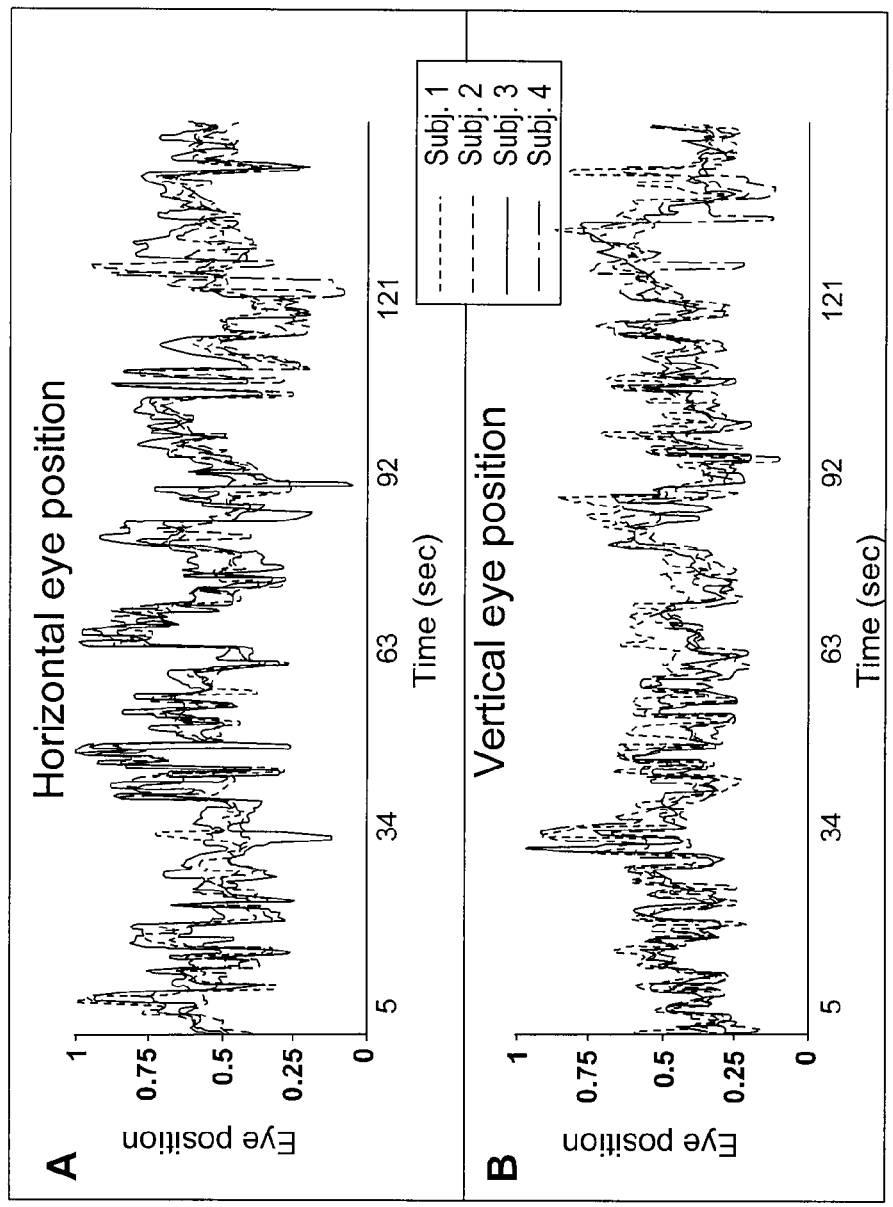
FIG. 4 are exemplary graphs used with an exemplary inter-subject correlation procedure associated with a subject's eye position in accordance with exemplary embodiments of the present disclosure.

As illustrated in the exemplary graphs of FIG. 4, for example, in addition to the reliable cortical response patterns illustrated in FIG. 3, the same film exerted considerable control over the subjects' behavior as measured by tracing their eye movements during the movie. The highly reproducible responses to the film demonstrate that some films can exert considerable control over the subjects' brain activity, including their behavior (e.g., eye movement).

For example, in the top portion of FIG. 4 (e.g., section "A"), horizontal eye positions are shown as recorded in an MRI scanner from four subjects during movie watching. The bottom portion of FIG. 4 (e.g., section "B") shows an example vertical eye position from the same subjects and movie. As can be seen in FIG. 4, there is a strikingly similar degree of agreement in the eye movements among the individual subjects.

Assessing Engagement Level for Different Films

An exemplary percentage of cortex exhibiting high ISC can provide a measure of the overall effectiveness, or collective engagement power, of a movie to induce similar responses across viewers, for example. The percentage of cortex exhibiting high ISC may be calculated by counting the percentage of voxels that pass the exemplary ISC statistical parametric mapping procedure (as described herein with respect to FIG. 2). The higher the percentage of cortex exhibiting high ISC, the more effective is the film in evoking similar responses across all viewers. For example, the ISC was used to assess the collective engagement power of four different films: 1) Sergio Leone's The Good, the Bad and the Ugly (1966); 2) A TV episode of Alfred Hitchcock Presents (Bang! You're Dead, 1961); 3) A TV episode of Larry David's Curb Your Enthusiasm (2000); 4) a self made video filmed by us in the Washington Square Park (2006). For two of these stimuli, GSR and eye movements were also measured.

Figure 5:
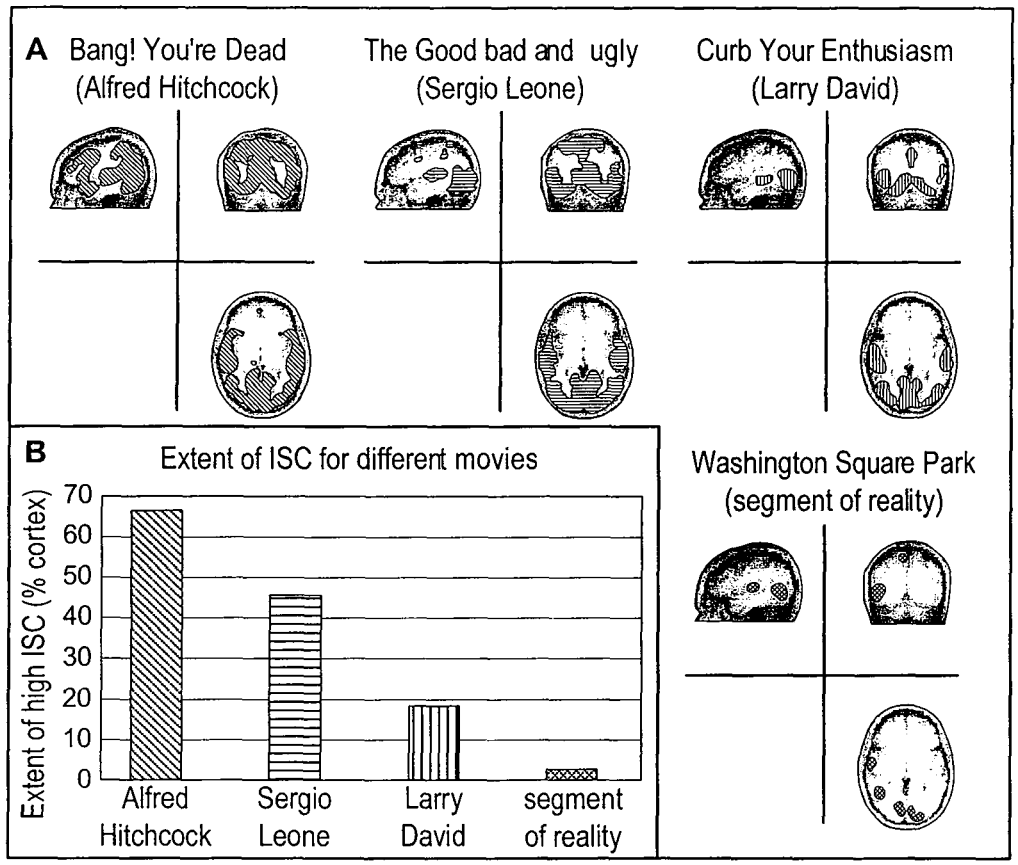
FIG. 5 are exemplary illustrations and graphs utilized with and generated using an exemplary inter-subject correlation procedure for different movies in accordance with exemplary embodiments of the present disclosure.

It is possible to calculate or determine the exemplary ISC for each of the four movies (using the exemplary procedure described herein and shown in FIG. 2). The exemplary ISC parametric map for each movie is shown in FIG. 5, for example. Certain shaded lines mark brain regions that exhibit high ISC in Hitchcock's TV episode. Other shaded lines mark brain regions that exhibit high ISC in Sergio Leone's movie. Still other shaded lines mark brain regions that exhibit high ISC in Larry David's TV episode. And yet further shaded lines mark brain regions that exhibit high ISC in an amateur video. The results demonstrate that each movie evoked a different level of ISC. The amateur video of Washington Square park (see, e.g., FIG. 5, lightest shaded line area) may evoke far less ISC than the commercial films. Moreover, even between the commercial movies and TV episodes, there are significant differences in the extent of the ISC (as opposed to the illustrations of FIG. 4, which show the other shaded lined areas).

In particular, FIG. 5 shows an exemplary illustration generated using the exemplary ISC for four different films: Alfred Hitchcock Presents: Bang! You're Dead, Sergio Leone's the Good, the Bad and the Ugly, Larry David's Curb Your Enthusiasm and the unedited, one-shot segment-of-reality video filmed in Washington Square Park. The three images in each panel depict the ISC in typical slices through the brain at each of the three cardinal orientations. FIG. 5 also shows an exemplary illustration of an extent of the exemplary ISC evoked by each movie segment as measured by the percentage of cortex that exhibited high ISC.

The exemplary percentage of cortex exhibiting high ISC can be determined in each of the 4 movies. This can provide a measurement as to the collective engagement power of each movie, for example. As shown in FIG. 5, the Hitchcock episode can evoke similar responses across all viewers in over 65% of the cortex, indicating a high level of control of this particular episode upon viewers' minds. The Hitchcock ability to orchestrate the responses of so many different brain regions during movie watching, turning them on and off at the same time across all viewers, provides neuroscientific evidence for Hitchcock's ability to master and manipulate viewers' minds. The high ISC was extensive (e.g., 45%) also for the Good, the Bad and the Ugly, but much less (e.g., 18%) for Curb Your Enthusiasm. Finally, the unstructured segment of reality induced high ISC only in small fraction of the cortex (less than 5%), mainly in early auditory and visual areas. The fact that different films and TV episodes evoke different levels of ISC can facilitate filmmakers and studios to assess the potency of a given product to "control" viewers' responses and reactions.

Assessing Exemplary Engagement Level for Different Film Components

The exemplary level of ISC within each brain area can provide a measurement regarding the effectiveness of different aspects of a film. Some of the mental faculties engaged with the processing of a film may differ across film genres (e.g., drama, thriller, comedy, etc.). A highly emotional film is likely to engage the emotional systems of the brain, for example, while a highly contemplative movie will likely engage regions of the brain involved in higher cognitive function. Even within the same movie, the processing of different scenes may rely on the operations of different brain regions.

For example, the exemplary ISC procedure can be used to assess the effectiveness of a movie sequence, separately, for each of several brain regions. The higher the ISC within each brain area the more effective is the stimulus for evoking reliable responses in this area. For example, high ISC in visual or auditory areas in response to a given movie sequence implies a high effectiveness of the visual image or soundtrack, respectively, upon viewers' visual or auditory percepts. Likewise, high ISC in brain areas related to emotion processes or cognitive processes assesses the effectiveness of a movie in controlling, respectively, viewers' emotions and thought processes.

Figure 6:
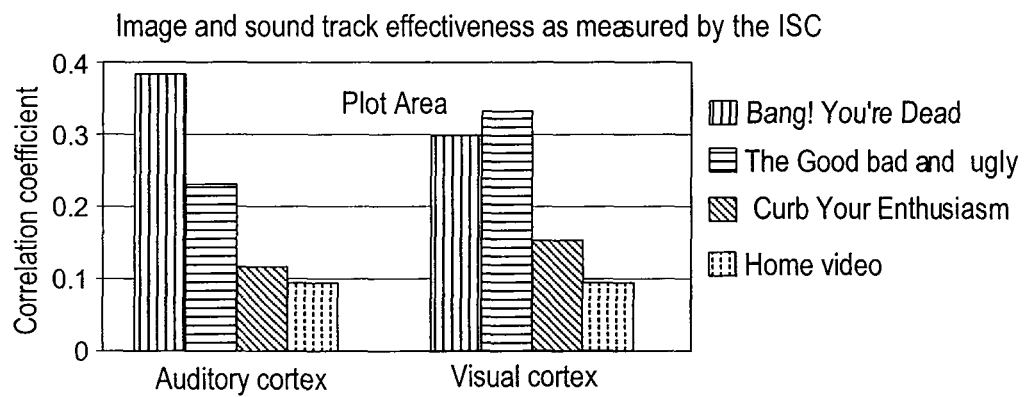
FIG. 6 are exemplary graphs illustrating degrees of an exemplary inter-subject correlation within the auditory and visual cortices in accordance with exemplary embodiments of the present disclosure.

FIG. 6 shows a graph of an exemplary ISC separately for visual and auditory areas across different movies. The effectiveness of the visual image and soundtrack differs for each of the movies. This procedure can provide the filmmaker with valuable information regarding the effectiveness of each aspect of the film. The exemplary illustration shows a degree of inter subject correlated voxels within the auditory and visual cortices. For example, the soundtrack for "Bang! You're Dead" induced the highest ISC in auditory cortex. In contrast, the visual images in The Good, the Bad and the Ugly" were slightly more effective in inducing high ISC in visual areas than "Bang! You're Dead". Finally the HBO TV sitcom video and the non-commercial (Home) video were less effective in controlling the brain activity in auditory and visual cortices.

Figure 7A:
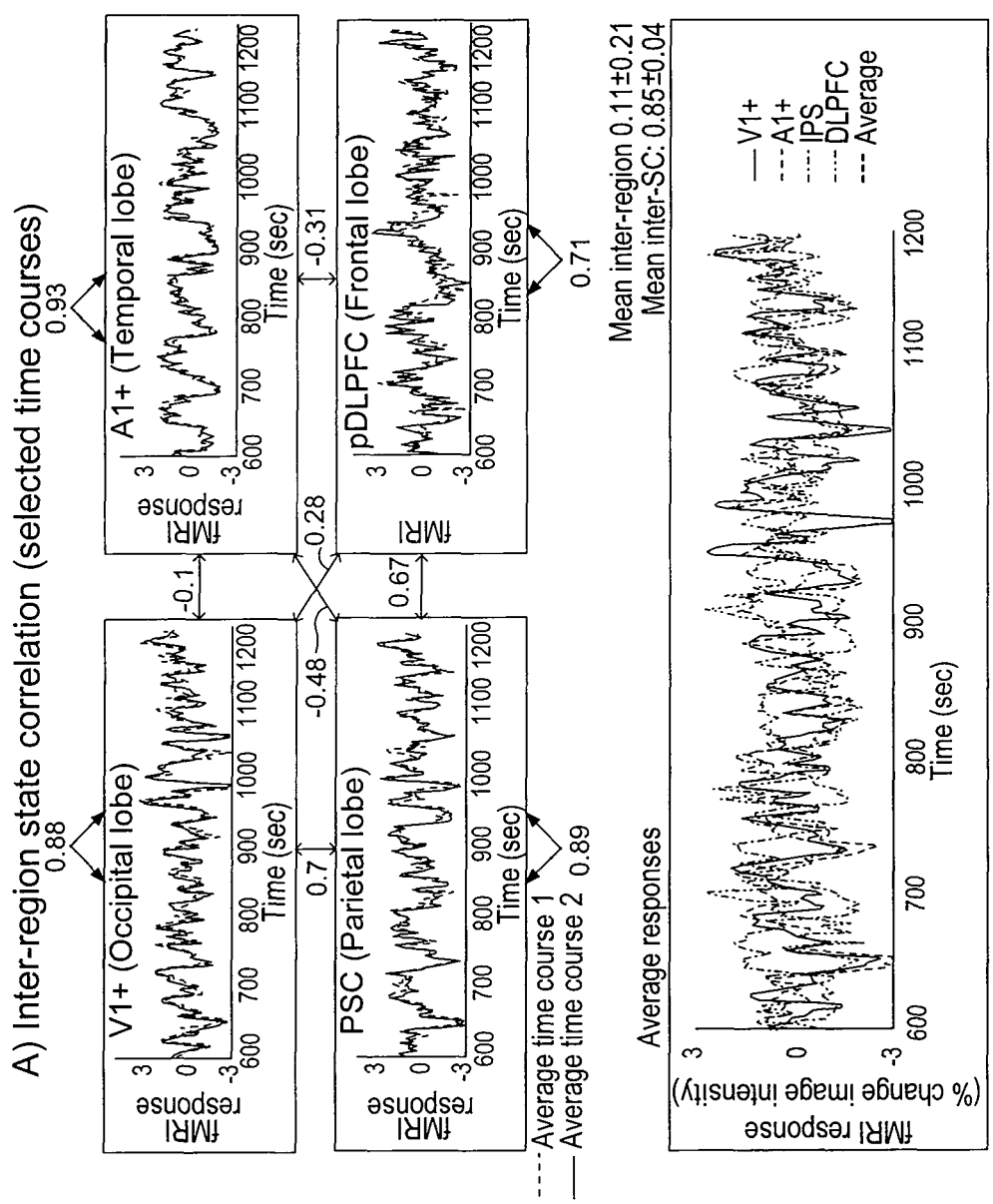
FIG. 7A is exemplary graphs illustrating degrees of an exemplary inter-subject correlation within regions over time in accordance with exemplary embodiments of the present disclosure.

Reliable responses (e.g., high ISC), although widespread, are selective such that they differ from one brain area to another. FIG. 7A illustrates exemplary graphs of the response time courses evoked by the Hitchcock TV episode, from four example brain regions: V1+ (a region in the vicinity of primary visual cortex), A1+ (a region in the vicinity of primary auditory cortex), PSC (a subregion in the post-central sulcus), and pDLPFC (a subregion of posterior, dorsolateral prefrontal cortex). The ISC was high within each of the four regions (e.g., mean within-region inter-SC=0.85±0.04), reflecting the reliable response time courses evoked by the stimulus. Nevertheless, each region also exhibited a unique response time course (e.g., mean inter-region correlation=0.11±0.21).

Figure 7B:
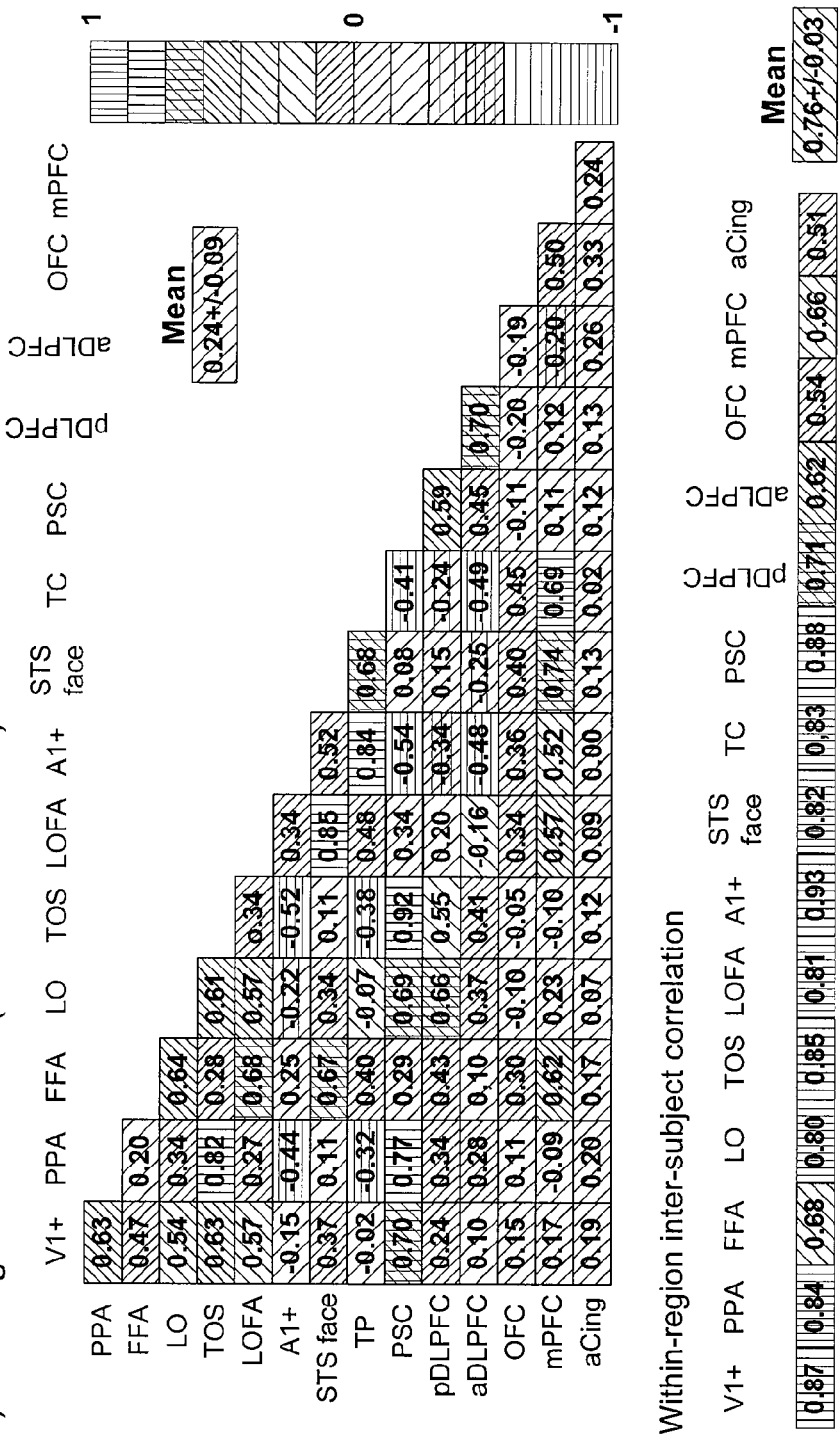
FIG. 7B is an example matrix and a table illustrating a degree of an exemplary inter-subject correlation in accordance with exemplary embodiments of the present disclosure.

FIG. 7B shows an exemplary matrix of inter-region correlations for 15 different brain areas, including visual cortical areas (V1+: a region in the vicinity of primary visual cortex; PPA: parahippocampal place area that responds more to buildings than objects or faces; FFA: fusiform face area that responds more to faces than objects or buildings; LO: lateral occipital area; LOFA: lateral occcipital face area that responds more to faces than objects or buildings; TOS: a subregion of the transverse occipital sulcus that responds more to buildings than objects or faces; STS: a subregion of the superior temporal sulcus; PSC: a subregion of the post-central sulcus), auditory areas (A1+: a region in the vicinity of primary auditory cortex; TP: a region in the vicinity of the temporal pole), and areas of prefrontal cortex (pDLPFC: a subregion of posterior dorsolataral prefrontal cortex; aDLPFC: a subregion of anterior dorsolataral prefrontal cortex; mPFC: a subregion of medial prefrontal cortex; OFC: a subregion of orbitofrontal cortex; aCing: a subregion of anterior cingulate cortex). Similar results were obtained for many other brain areas.

The exemplary response time courses differed across brain regions. For example, A1+ was positively correlated with some temporal and frontal areas, but uncorrelated or negatively correlated with occipital and parietal areas. Posterior DLPFC exhibited a completely different profile of correlations, exhibiting some positive correlations with occipital and parietal areas, and negative correlations with temporal regions. Such measurements of response correlations between areas (e.g., also can be termed "functional connectivity") have been used to infer functional interactions between brain regions. However, they can be used herein to demonstrate that the response time course within each region was unique and distinctive, yet highly reliable across viewers. The selectivity of responses can demonstrate that the bulk of inter- and intra-SC within each brain cannot be simply attributed to non-specific, spatially global effects like arousal.

In particular, FIG. 7A shows an exemplary graph of responses evoked by the Hitchcock episode, from each of four distinct brain regions. With respect to the upper panels, response time courses averaged separately across each brain region and separately for each of two groups of subjects (group 1, n=12; group 2, n=11). FIG. 7A also shows the exemplary correlation coefficients between the two response time courses within each brain region, across the two groups of subjects, as well as the correlation coefficients across brain regions. With respect to the lower illustration of FIG. 7A, the mean response time courses for each brain region are shown as averaged across all 23 subjects.

FIG. 7B shows an example of the inter-region correlations and within-region inter-subject correlations for 15 example brain areas. In the upper panel of FIG. 7B is a matrix of inter-region correlations computed by first averaging across all 23 subjects. Shown in the lower section of the figure is within-region inter-subject correlations computed by first averaging the response time courses separately for the two groups of subjects, and then computing the correlation coefficients between the two resulting response time courses within each brain region. The different shaded areas can indicate the various levels of strength of the correlation coefficients.

Exemplary ISC as Neuroscience-based Editing System

Comparing the level of ISC across different working versions of the same film (rough cuts) can provide filmmakers and studios with a new assessment tool for choosing between them. For example, re-editing of the exact same list of shots can have a dramatic effect on the ISC in brain areas which accumulate information across shots and process the movie as a whole. Thus, it is possible to use the exemplary ISC to test the effectiveness of different versions of the stimuli (e.g., different versions or cuts of the same movie). The higher the ISC for a given version, the more effective it generally is in evoking similar response patterns across all viewers.

Moreover, additional information about audience engagement in each segment of the movie can be obtained by computing or determining the exemplary ISC separately for different scenes in the movie. FIG. 8, for example, shows an illustration of an exemplary graph of the ISC across subjects for each 2 minute segment of the Hitchcock movie. This can provide a dynamic, time-varying measure of collective engagement during the movie. In this example, the exemplary ISC increases dramatically near the end of the movie, corresponding to the climactic scene. Such a time-varying measure can provides a new neuro-editing tool for assessing the moment to moment impact of a given film. Changes in the engagement over time may be related to the director's intentions (as in this example) or unintentional. The measurement of the evolution of ISC over time can provide filmmakers with information about the level of engagement in each scene or sequences of scenes. Detecting an unintentional reduction in the ISC at a particular moment of the movie may point to the need to further edit the scene to achieve the desired effect.

The temporal evolution of ISC can be refined further by measuring it separately for each of several brain regions. For example, FIG. 7A also shows an exemplary graph of the exemplary ISC over time in early auditory cortex during the Hitchcock movie. The ISC in auditory cortex can be relatively high (average ISC value of about 0.67) throughout the movie, attesting to the effectiveness of this particular soundtrack to induce similar responses across viewers throughout the entire duration of the film. However, a reduction (less than about 0.45) in the ISC occurred around 280 sec, 330 sec and 500 sec after the beginning of the film. If such a reduction in the ISC may be unintentional and undesirable, then such information can be used for further adjusting these particular segments of the soundtrack, for example.

Assessing Exemplary Engagement Level across Different Target Groups

Comparing the level of ISC across groups can provide filmmakers and studios with a new assessment of how the same product affects different target groups. The discussion herein above has largely been based on the similarity in response time courses across all viewers while watching the same movie, ignoring individual and inter-group differences. The subjects were primarily university college students, composed of approximately 50% men and 50% women, and approximately 30% minorities. Thus, the results discussed above represent the average similarity across this largely heterogeneous group. Such similarity is expected given that all viewers are still part of a similar age group, are all experienced film viewers, and overall should perceive and interpret this particular set of films in a similar way.

However, such similarities notwithstanding, the effect of a given film can vary across different individuals and target groups. Different spectators may perceive and interpret the same situation in various, and sometimes opposing ways. Thus, the same or similar computational steps or procedures which are described above with reference to FIG. 2 can also be used as a measurement of systematic differences in how various groups of individuals (defined by, e.g., age, gender, sexual preference, ethnicity, cultural background, etc.) respond to the same film. Measuring the exemplary ISC within each of the designated groups can identify brain regions in which the response time courses are similar across members of the group. Measuring the ISC between groups can identify brain regions in which the response time courses were similar across members of the two groups. Subtracting the within group ISC map from the between groups ISC map can reveal brain areas in which the responses were consistent within a group, but different between groups. This can be used to assess the impact of a given film on different target groups (e.g., teenagers vs. adults), for example. This type of functional analysis does not have to make presumptions about differences between groups. Rather, it can facilitate an unbiased objective mapping of all the differences in the patterns of brain activations between groups for a given movie.

Assessing Exemplary Engagement Level for Other Kinds of Media

Various examples of ISCs can be employed to measure the collective engagement and effectiveness of different types of media. The uses of certain examples of ISC have been discussed for assessing the effectiveness and collective engagement power of films. However, the same or similar example computational procedures, which are described herein with reference to FIG. 2, can be used to assess different types of media, including, but not limited to, e.g., print ads, TV commercials, political speeches, audio-books, pop-songs and other types of music.

For example, as shown for the illustrations of FIG. 9, it is possible to compare the ISC for a visually guided movie from which we removed the soundtrack (Charlie Chaplin's classic film City Lights, 1931) with the ISC for an audio-book soundtrack (Lewis Carroll's classic book Alice in Wonderland). The results can reveal a strong specificity, in which visual cortex was highly correlated across viewers during the silent film (as shown in the illustrations of FIG. 9), but not during story listening, and vice versa for auditory cortex (again, as shown in FIG. 9). This comparison also revealed overlapping regions of high ISC (as shown in FIG. 9) in the superior temporal sulcus (STS), temporal-parietal junction (TPJ), and part of the left intraparietal sulcus (IPS). These results may facilitate an assessment of the reliability of brain responses for audio-books and other audio-based media (as music, lectures and political speeches).

The neuroscience-based editing system described herein for application with films can be utilized as well for any of these other media, including music, advertisements, and media not yet developed to which the exemplary embodiments of the present disclosure may be applicable. Likewise, the exemplary embodiments of the method and procedure described above for assessing differences between groups can also be applied to these other media.

Figure 10:
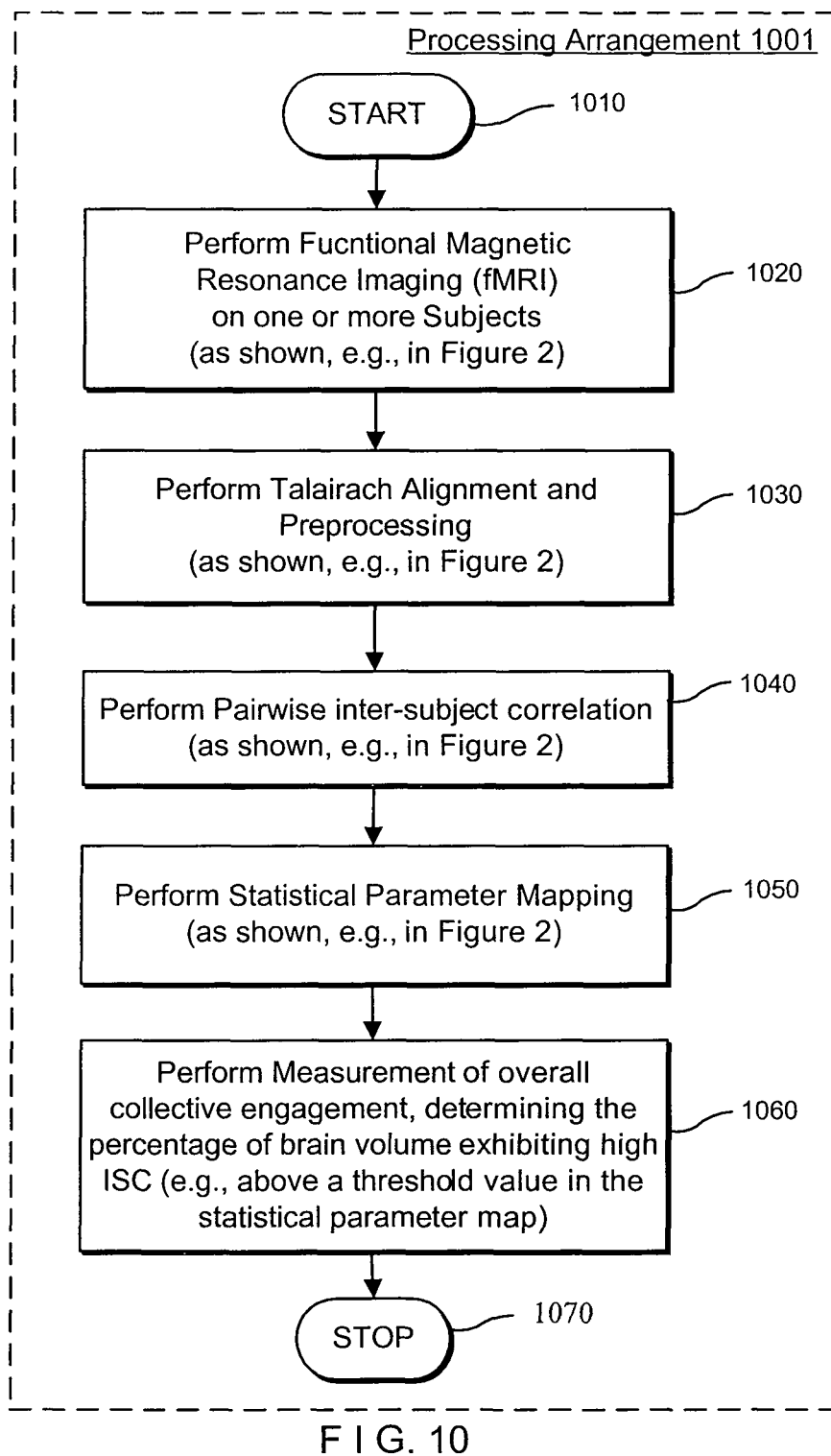
FIG. 10 is a flow diagram of an exemplary procedure for assessing an effect of a stimulus using an inter-subject correlation (ISC) procedure in accordance with the present disclosure.

FIG. 10 shows a flow diagram of an exemplary procedure for assessing the effect of a stimulus using inter-subject correlation in accordance with the present disclosure. As shown in FIG. 10, the exemplary procedure can be executed on and/or by a processing arrangement 1001 (e.g., a microprocessor, or a collection thereof). Starting at 1010, the exemplary procedure, in 1020, performs an exemplary functional magnetic resonance imaging (fMRI) procedure on one or more subjects (as illustrated, e.g., in FIG. 2). In 1030, the exemplary procedure can perform Talairach alignment and preprocessing (also illustrated, e.g., in FIG. 2). The exemplary procedure then, in 1040, can perform pair-wise inter-subject correlation (also illustrated, e.g., in FIG. 2). Next, in 1050, the exemplary procedure may perform a statistical parameter mapping (also illustrated, e.g., in FIG. 2). The exemplary procedure then, in 1060, performs measurement of overall collective engagement, thus determining the percentage of brain volume exhibiting high ISC (e.g., above a threshold value in the statistical parameter map).

Similar exemplary procedures are discussed above, which can differ primarily with respect to measuring the effectiveness. For example, in one such exemplary procedure, the effectiveness can be measured by computing or determining the extent (e.g., a percentage of volume) and magnitude of ISC in each of a number of brain areas. The exemplary measurements from each brain area assess effectiveness for different aspects of a movie, for example.

In another exemplary procedure, the performance of pairwise inter-subject correlation can optionally be computed separately for different scenes or for overlapping time windows, for example. Similarly, statistical parameter mapping can be optionally performed for each scene or time window. Collective engagement over time can be achieved through determining the percentage of cortex exhibiting high ISC, above a threshold value in the statistical parameter map, separately for each scene or time window. The measurement of effectiveness can be determined by the extent (percentage of volume) and magnitude of ISC in each of a number of brain areas, separately for each scene or time window.

It is also possible to re-edit or choose between different working versions based on effectiveness measures by identifying scenes that are not sufficiently effective (e.g., do not exceed a threshold value on the effectiveness measures) and re-edit those scenes accordingly. In addition, working versions of a scene or of an entire film that evokes the largest effectiveness measures throughout the entire duration or during particular scenes can be selected. Similarly to above, performance of pair-wise inter-subject correlation can optionally be computed separately for different scenes or for overlapping time windows, for example. Statistical parameter mapping can be optionally performed for each scene or time window, and separately for each target group. A collective engagement over time can be achieved through determining the percentage of cortex exhibiting high ISC, above a threshold value in the statistical parameter map, separately for each scene or time window, and separately for each target group. Measurement of effectiveness can be determined by the extent (percentage of volume) and magnitude of ISC in each of a number of brain areas, separately for each scene or time window, and separately for each target group, for example.

Figure 11:
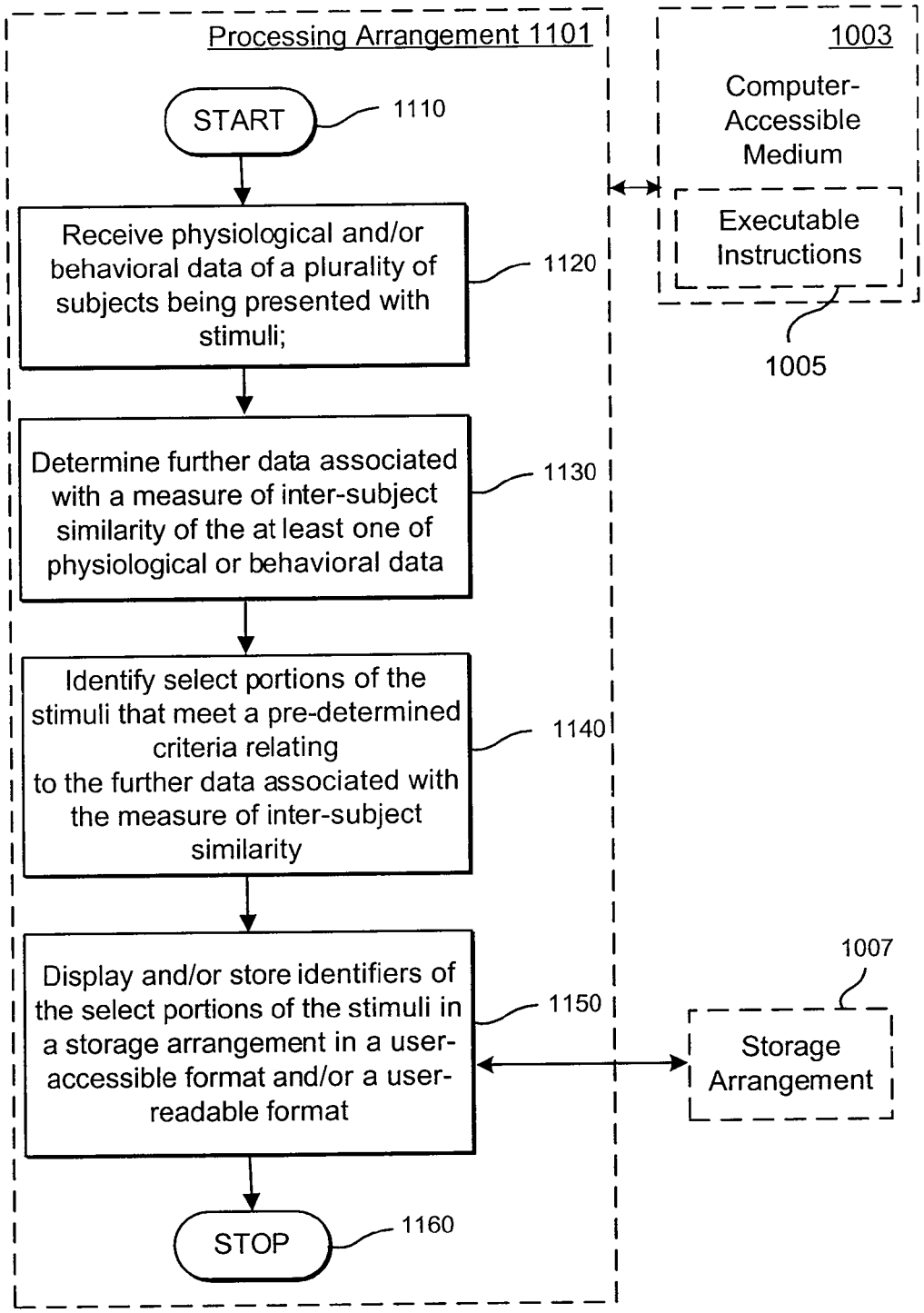
FIG. 11 is a block diagram of an exemplary system configured in accordance with the present disclosure for assessing an effect of a stimulus using the ISC procedure.

FIG. 11 shows a block diagram of an exemplary system configured in accordance with the present disclosure for assessing an effect of a stimulus using the exemplary ISC procedure. As shown in FIG. 11, a computer-accessible medium 1003 (i.e., storage device such as hard disk, floppy disk, memory stick, RAM, ROM, etc., or a collection thereof) can be provided (in communication with the processing arrangement 1001), that contains executable instructions 1005 thereon. For example, when the processing arrangement 1001 accesses the computer-accessible medium 1003, and retrieves therefrom and then executes the instructions 1005, the processing arrangement 1001 can be configured to receive neuronal, physiological and/or behavioral data one or more subjects being presented with stimuli in block 1120, determine further data associated with a measure of inter-subject similarity of the neuronal, physiological and/or behavioral data in block 1130, and identify select portions of the stimuli that meet a pre-determined criteria relating to the further data associated with the measure of inter-subject similarity in block 1140. Further, the processing arrangement, based on the instructions 1005, can be configured to display and/or store identifiers of select portions of the stimuli in a storage arrangement 1007 in a user-accessible format and/or a user-readable format in block 1150.

Figure 12:
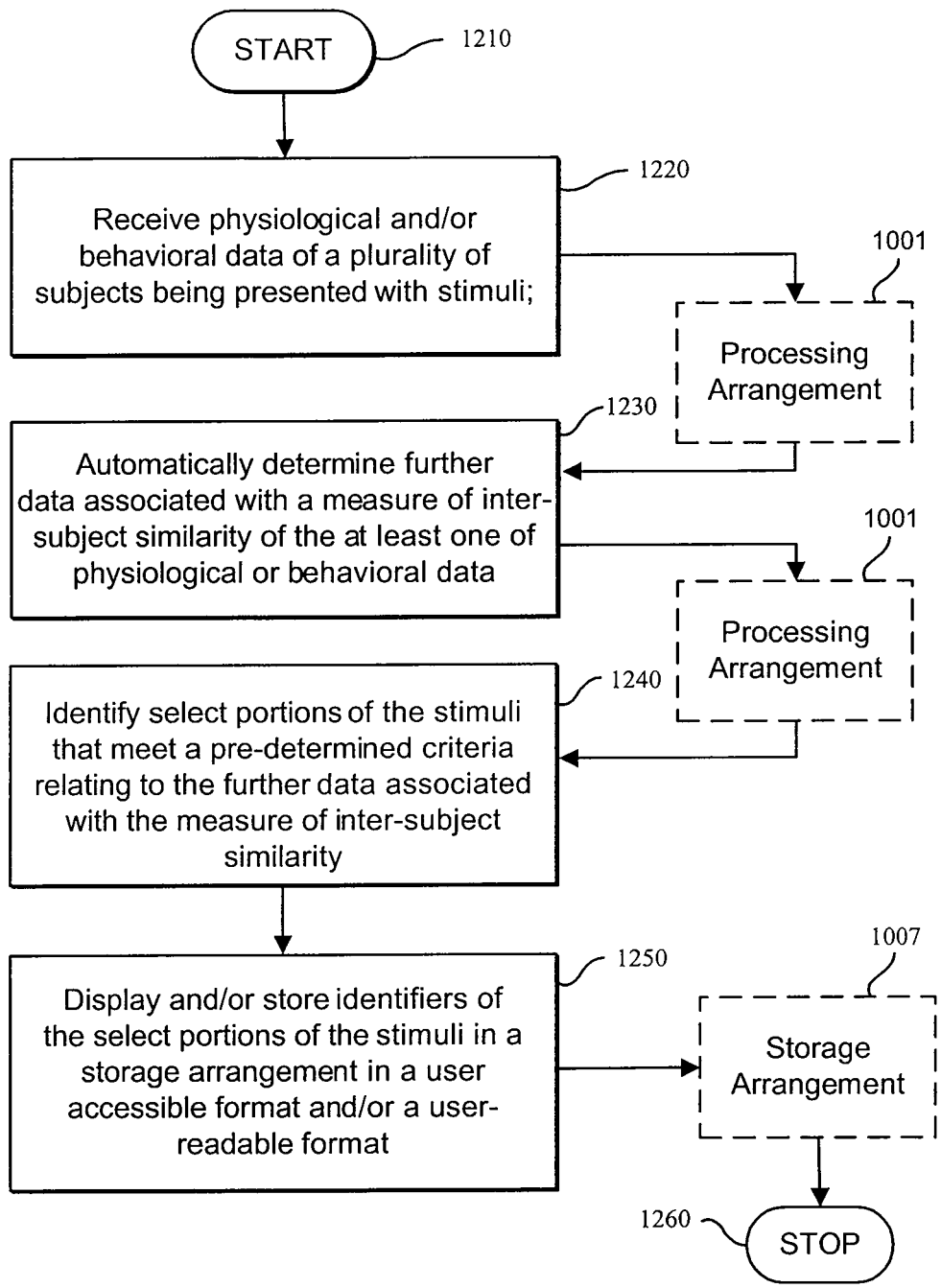
FIG. 12 is a combination flow and block diagram illustrating an exemplary method in accordance with the present disclosure for assessing an effect of a stimulus using the ISC procedure.

FIG. 12 is a combination flow and block diagram illustrating an exemplary method/procedure in accordance with the present disclosure for measuring a level and/or details of how engaging, effective and memorable a stimulus is based on, e.g., information associated with one or more subjects' neuronal, physiological and/or behavioral responses to the stimulus. As shown in FIG. 12, the exemplary method/procedure begins in block 1210 and then proceeds to block 1220 (receiving physiological and/or behavioral data of one or more subjects being presented with stimuli). The exemplary method/procedure then proceeds to block 1230 (using a processing arrangement 1001, automatically determining further data associated with a measure of inter-subject similarity of the physiological and/or behavioral data). Next, the exemplary method can proceed to block 1240 (using the processing arrangement 1001, automatically identifying select portions of the stimuli that meet a pre-determined criteria relating to the further data associated with the measure of inter-subject similarity). The exemplary method can then proceed to 1250 (displaying and/or storing identifiers of select portions of the stimuli in a storage arrangement 1007 in a user-accessible format and/or a user-readable format). The exemplary method then stops at 1260.

There are a number of possible variations and extensions to each of the above exemplary procedures that can utilize the concepts described herein. For example, following is a partial and non-limiting list of these non-limiting variations and extensions:

A. Data can be acquired using any number of brain imaging or physiological or behavioral monitoring devices including, but not limited to, fMRI, PET, SPECT, fNIRS, optical imaging, EEG, MEG, GSR, eye movements, pupil size, and motion capture of head movements, body movements, and facial expressions.

B. Data can be aligned across subjects using any of a number of atlases or coordinate frames including, but not limited to, Talairach, MNI, and surface-based alignment. Variations of the example procedures that do not require alignment can also be utilized.

C. The ISC can be applied to data acquired with any combination of the above devices, or any other devices that provide time series of measurements of brain activity or physiological responses or behavioral responses.

D. The exemplary ISC calculation can be replaced by any number of computational methods for assessing the similarity between the time series from a pair or group of subjects. Such exemplary computational methods include, but are not limited to, coherence, canonical correlation, general linear model, mutual information, principal components analysis, and independent components analysis.

E. Instead of inter-subject correlation (which measure the shared responses across individuals), exemplary methods can measure the reliable intra-subject correlation within the same subject (which measure the reliable idiosyncratic responses within an individual), by comparing response time courses evoked by repeated presentations of the same stimulus within the same subject, for example. The exemplary embodiment of the intra-subject correlation can be a useful measure of the reliability of brain activity and behavior (e.g., eye movements), and hence as a maker for the potency of media to evoke a unique neural and behavioral responses within a specific viewer and listeners.

F. Further examples can include, e.g., using inter-subject correlation (or any of a plurality of other measures of similarity) to assess which aspects of physiological and behavioral response time courses are indicative/predictive of whether or not a group of individuals share the same preferences for media.

G. According to other exemplary embodiments, it is possible to measure eye movements for a group of individuals while they watch the movie using the system, method and computer-accessible medium described herein. This can be done, e.g., by setting up a particular screening room with eye trackers for each of, e.g., 50 individuals, simultaneously. The average percentage of people who fixate the product and the average amount of time of fixation can be measured. Then, when the movie is released, the box office sales can be multiplied by the percentage of people who look at the product and charge the advertiser accordingly (e.g., a certain amount per fixation). Further, it is possible to combine eye tracking information (optionally with other modalities such as fMRI, etc.) with measures of inter-subject similarity to assess, e.g., product placement or advertising and even to price product accordingly.

The foregoing merely illustrates the principles of the present disclosure. Various modifications and alterations to the described example embodiments will be apparent to those skilled in the art in view of the teachings herein. It will thus be appreciated that those skilled in the art will be able to devise numerous systems, arrangements and methods which, although not explicitly shown or described herein, embody the principles of the present disclosure and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. A non-transitory computer-accessible medium containing executable instructions thereon, wherein when a processing arrangement executes the instructions, the processing arrangement is configured to perform procedures comprising:
   receive first information associated with at least one particular version of a stimuli;
   receive second information associated with least one further version of the stimuli;
   determine an inter-subject correlation (ISC) for each of the first information and the second information;
   select at least one of the at least one particular version or the at least one further version based on the determined ISC; and
   at least one of display or store identifiers of particular portions of the stimuli in a storage arrangement in at least one of a user-accessible format or a user-readable format;
   wherein the identifiers are configured to provide to at least one of a user or a computer system access to certain portions of at least one of a film or a video, and wherein the processing arrangement is further configured to, using the access, at least one of edit or alter the certain portions of the at least one of the film or the video based on the selected at least one particular version or the at least one further version.

2. The computer-accessible medium according to claim 1, wherein the first information and the second information include at least one of neuronal data, physiological data or behavioral data of a plurality of subjects presented with the stimuli.

3. The computer-accessible medium according to claim 2, wherein the at least one of the neuronal data, the physiological data or the behavioral data is a data associated with at least one of MRI, PET, SPECT, fNIRS, optical imaging, EEG, MEG or GSR techniques, eye movements, a pupil size, or a motion capture of at least one of a head movement, a body movement or a facial expression.

4. The computer-accessible medium according to claim 1, wherein the stimuli includes at least one of a visual stimuli, an auditory stimuli, a tactile stimuli, an olfactory stimuli or a gustatory stimuli.

5. The computer-accessible medium according to claim 1, wherein the processing arrangement is further configured to determine the ISC using at least one of a correlation, a general linear model, a canonical correlation, a coherence, a mutual information, principal component analysis or an independent component analysis (ICA).

6. The computer-accessible medium according to claim 1, wherein the stimuli is a recorded stimuli having a form of at least one of an audio recording, a film, a video or an advertisement.

7. The computer-accessible medium according to claim 1, wherein the identifiers include at least one of (i) one or more frame numbers, or (ii) one or more points in time referencing certain portions of at least one of an audio recording, a film, a video or an advertisement.

8. The computer-accessible medium according to claim 1, wherein the identifiers include one or more points in time referencing select portions of an audio recording.

9. The computer-accessible medium according to claim 1, wherein the ISC relates to an activity of at least one of a visual cortex, an auditory cortex, a language area, an anterior cingulate, an anterior dorsolateral prefrontal cortex, a posterior dorsolateral prefrontal cortex, a frontal eye field, a medial prefrontal cortex, an orbito-frontal cortex, a fusiform face area, a parahippoampal place area, a lateral occipital cortex, a lateral occipital face area, an MT complex, a superior temporal sulcus, a superior temporal face area, a temporal pole, a temporal-parietal junction, an intraparietal sulcus, a mirror system area, a precuneus, a ventral premotor area, a dorsal premotor area, a medial temporal lobe, a hippocampus, an entorhinal cortex, a perirhinal cortex, an amygdala, a basal ganglia, a striatum, a putamen, a caudate, a pallidum, a substantia nigra or a cerebellum of a brain of at least one subject presented with the stimuli.

10. The computer-accessible medium according to claim 1, wherein the ISC is independent of a reliance on a particular regional functional specialization of a brain.

11. The computer-accessible medium according to claim 1, wherein the processing arrangement is further configured to compare between the first information and the second information associated with two or more demographic groups of subjects presented with the stimuli.

12. The computer-accessible medium according to claim 1, wherein the processing arrangement is further configured to utilize the first information and the second information to assess at least one of a memorability, an engagement, an effectiveness, a cognition or an emotional response.

13. The computer-accessible medium according to claim 1, wherein the processing arrangement is configured to select the at least one particular version or the at least one further version as a function of a percentage of a cortex that meets a predetermined criteria of a similarity of at least one subject that is presented with the stimuli.

14. The computer-accessible medium according to claim 1, wherein the processing arrangement is configured to select the at least one particular version or the at least one further version as a function of a magnitude of a similarity in a plurality of brain areas of at least one subject that is presented with the stimuli.

15. The computer-accessible medium according to claim 1, wherein the processing arrangement is configured to select the at least one particular version or the at least one further version based on a sequence of at least one of movie scenes or video scenes with at least one of overlapping or non-overlapping time windows.

16. The computer-accessible medium according to claim 15, wherein the processing arrangement is further configured to measure the ISC separately for the at least one of the movie scenes or the video scenes.

17. The computer-accessible medium according to claim 1, wherein the determined ISC has a first ISC associated with the at least particular version and a second ISC associated with the at least on further version, and wherein the processing arrangement performs the selection based on a higher one of the first ISC or the second ISC.

18. A system for measuring a level and details of at least one of how engaging, effective or memorable a stimulus is based on information associated with at least one of one or more neuronal, physiological or behavioral responses of one or more of subjects to the stimulus, comprising:
a non-transitory computer-accessible medium having executable instructions thereon, wherein when a processing arrangement executes the instructions, the processing arrangement is configured to:
receive first information associated with at least one particular version of a stimuli;
receive second information associated with at least one further version of the stimuli;
determine an inter-subject correlation (ISC) for the first information and the second information;
select at least one of the at least one particular version or the at least one further version based on the ISC; and
at least one of display or store identifiers of particular portions of the stimuli in a storage arrangement in at least one of a user-accessible format or a user-readable format;
wherein the identifiers are configured to provide to at least one of a user or a computer system access to certain portions of at least one of a film or a video, and wherein the processing arrangement is further configured to, using the access, at least one of edit or alter the certain portions of the at least one of the film or the video based on the selected at least one particular version or the at least one further version.

19. The system according to claim 18, wherein the first information and the second information include at least one of neuronal data, physiological data or behavioral data of a plurality of subjects presented with the stimuli.

20. The system according to claim 19, wherein the at least one of the neuronal data, the physiological data or the behavioral data is a data associated with at least one of MRI, PET, SPECT, fNIRS, optical imaging, EEG, MEG or GSR techniques, eye movements, a pupil size, or a motion capture of at least one of a head movement, a body movement or a facial expression.

21. The system according to claim 18, wherein the selection is based on the ISC for one at least one of the at least one particular version or the at least one further version being higher than the ISC for the other one of at least one particular version or the at least one further version.

22. A method for measuring a level and details of how engaging, effective and memorable a stimulus is based on information associated with at least one of neuronal, physiological or behavioral responses of one or more of subjects to the stimulus, comprising:
receiving first information associated with at least one particular version of a stimuli;
receiving second information associated with at least one further version of the stimuli;
determining an inter-subject correlation (ISC) for the first information and the second information;
using a processing arrangement, selecting at least one of the at least one particular version or the at least one further version based on the ISC; and
at least one of displaying or storing identifiers of particular portions of the stimuli in a storage arrangement in at least one of a user-accessible format or a user-readable format;
wherein the identifiers are configured to provide to at least one of a user or a computer system access to certain portions of at least one of a film or a video, and wherein the processing arrangement is further configured to, using the access, at least one of edit or alter the certain portions of the at least one of the film or the video based on the selected at least one particular version or the at least one further version.

23. The method according to claim 22, wherein the first information and the second information include at least one of neuronal data, physiological data or behavioral data of a plurality of subjects presented with the stimuli.

24. The method according to claim 23, wherein the at least one of the neuronal data, the physiological data or the behavioral data is a data associated with at least one of MRI, PET, SPECT, fNIRS, optical imaging, EEG, MEG or GSR techniques, eye movements, a pupil size, or a motion capture of at least one of a head movement, a body movement or a facial expression.

25. The method according to claim 22, wherein the selection is based on the ISC for one at least one of the at least one particular version or the at least one further version being higher than the ISC for the other one of at least one particular version or the at least one further version.

26. A non-transitory computer-accessible medium containing executable instructions thereon, wherein when a processing arrangement executes the instructions, the processing arrangement is configured to perform procedures comprising:
receive first information associated with at least one particular version of a stimuli;
receive second information associated with least one further version of the stimuli;
determine an inter-subject correlation (ISC) for each of the first information and the second information;
select at least one of the at least one particular version or the at least one further version based on the determined ISC; and
at least one of display or store identifiers of particular portions of the stimuli in a storage arrangement in at least one of a user-accessible format or a user-readable format;
wherein the identifiers are configured to provide to at least one of a user or a computer system access to certain portions of the at least one particular version or the at least one further version, and wherein the processing arrangement is further configured to, using the access, at least one of edit or alter the certain portions the at least one particular version or the at least one further version based on the selected at least one particular version or the at least one further version.

27. The computer-accessible medium of claim 26, wherein the at least one particular version or the at least one further version is an audio recording.

28. The computer-accessible medium according to claim 27, wherein the identifiers include one or more points in time referencing the certain select portions of the at least one audio recording.

29. The computer-accessible medium according to claim 26, wherein the first information and the second information include at least one of neuronal data, physiological data or behavioral data of a plurality of subjects presented with the stimuli.

30. The computer-accessible medium according to claim 26, wherein the processing arrangement is further configured to determine the ISC using at least one of a correlation, a general linear model, a canonical correlation, a coherence, a mutual information, a principal component analysis or an independent component analysis (ICA).

31. A system for measuring a level and details of at least one of how engaging, effective or memorable a stimulus is based on information associated with at least one of one or more neuronal, physiological or behavioral responses of one or more of subjects to the stimulus, comprising:
- a non-transitory computer-accessible medium having executable instructions thereon, wherein when a processing arrangement executes the instructions, the processing arrangement is configured to:
- receive first information associated with at least one particular version of a stimuli;
- receive second information associated with least one further version of the stimuli;
- determine an inter-subject correlation (ISC) for each of the first information and the second information;
- select at least one of the at least one particular version or the at least one further version based on the determined ISC; and
- at least one of display or store identifiers of particular portions of the stimuli in a storage arrangement in at least one of a user-accessible format or a user-readable format;
- wherein the identifiers are configured to provide to at least one of a user or a computer system access to certain portions of the at least one particular version or the at least one further version, and wherein the processing arrangement is further configured to, using the access, at least one of edit or alter the certain portions the at least one particular version or the at least one further version based on the selected at least one particular version or the at least one further version.

32. The system of claim 31, wherein the at least one particular version or the at least one further version is an audio recording.

33. The system according to claim 32, wherein the identifiers include one or more points in time referencing the certain select portions of the at least one audio recording.

34. The system according to claim 31, wherein the first information and the second information include at least one of neuronal data, physiological data or behavioral data of a plurality of subjects presented with the stimuli.

35. The system according to claim 31, wherein the processing arrangement is further configured to determine the ISC using at least one of a correlation, a general linear model, a canonical correlation, a coherence, a mutual information, a principal component analysis or an independent component analysis (ICA).

36. A method for measuring a level and details of how engaging, effective and memorable a stimulus is based on information associated with at least one of neuronal, physiological or behavioral responses of one or more of subjects to the stimulus, comprising:
- receiving first information associated with at least one particular version of a stimuli;
- receiving second information associated with least one further version of the stimuli;
- determining an inter-subject correlation (ISC) for each of the first information and the second information;
- using a processing arrangement, selecting at least one of the at least one particular version or the at least one further version based on the determined ISC; and
- at least one of displaying or storing identifiers of particular portions of the stimuli in a storage arrangement in at least one of a user-accessible format or a user-readable format;
- wherein the identifiers are configured to provide to at least one of a user or a computer system access to certain portions of the at least one particular version or the at least one further version, and wherein the processing arrangement is further configured to, using the access, at least one of edit or alter the certain portions the at least one particular version or the at least one further version based on the selected at least one particular version or the at least one further version.

37. The method of claim 36, wherein the at least one particular version or the at least one further version is an audio recording.

38. The method according to claim 37, wherein the identifiers include one or more points in time referencing the certain select portions of the at least one audio recording.

39. The method according to claim 36, wherein the first information and the second information include at least one of neuronal data, physiological data or behavioral data of a plurality of subjects presented with the stimuli.

40. The method according to claim 36, further comprising determining the ISC using at least one of a correlation, a general linear model, a canonical correlation, a coherence, a mutual information, a principal component analysis or an independent component analysis (ICA).

* * * * *